United States Patent [19]

Kollar

[11] 4,337,371

[45] Jun. 29, 1982

[54] PRODUCTION OF ETHYLENE GLYCOL BY REACTION OF METHANOL, AN ORGANIC PEROXIDE AND FORMALDEHYDE

[75] Inventor: John Kollar, Wyckoff, N.J.

[73] Assignee: Celanese Corporation, New York, N.Y.

[21] Appl. No.: 183,537

[22] Filed: Sep. 2, 1980

[51] Int. Cl.³ .............................................. C07C 31/20
[52] U.S. Cl. ...................................................... 568/852
[58] Field of Search ......................................... 568/852

[56] References Cited

PUBLICATIONS

Oyama, "J. Org. Chem.", 30, Jul. 1965, pp. 2429–2432.

Primary Examiner—Joseph E. Evans
Attorney, Agent, or Firm—Linn I. Grim

[57] ABSTRACT

Ethylene glycol is prepared by reacting methanol, formaldehyde and no more than 6 weight percent based on the feed composition of an organic peroxide in the presence of water. The organic peroxide has the formula $R\text{-}O\text{-}O\text{-}R^1$ wherein R and $R^1$ are each an alkyl or aralkyl group having 3 to 12 carbon atoms.

8 Claims, No Drawings

PRODUCTION OF ETHYLENE GLYCOL BY REACTION OF METHANOL, AN ORGANIC PEROXIDE AND FORMALDEHYDE

This invention relates to a novel process for producing ethylene glycol.

Ethylene glycol, or 1,2-ethanediol, whose structural formula can be written as $CH_2OHCH_2OH$, is one of today's more important industrial chemicals. Its uses range from the well-known to the obscure. They include use in automotive coolant and antifreeze solutions, which in 1979 accounted for an estimated 1.9 billion pounds of the estimated 4.2 billion pounds of ethylene glucol produced in the United States, as a heat-transfer agent in refrigeration, and as an ingredient of deicing fluids for airport runways.

Ethylene glycol's uses as a chemical intermediate include its incorporation as an essential constituent in polyester fibers, films and bottle resins. Polyester fiber use alone amounted to an estimated 1.6 billion pounds of ethylene glycol in this country in 1979.

Ethylene glycol is also an important industrial solvent and extractant. As a solvent, for example, it is used with cellulose ethers and esters, especially cellophane, in lacquers, printing inks and adhesives.

There have been various industrial methods of synthesizing ethylene glycol. One of these involves initially reacting ethylene with hypochlorous acid to form ethylene chlorohydrin; see, for example U.S. Pat. Nos. 1,456,916 to Curme et al, issued May 29, 1923, and 1,456,959 to Young, issued May 29, 1923. Ethylene chlorohydrin may then be converted directly to ethylene glycol by hydrolysis in the presence of sodium bicarbonate; see U.S. Pat. No. 1,442,386 to Curme et al, issued Jan. 16, 1923.

Another important method of producing ethylene glycol, and one in common use today, involves direct oxidation of ethylene to ethylene oxide in the presence of a catalyst (see for example, U.S. Pat. No. 1,998,878 and U.S. Pat. Nos. Re. 20,370 and Re. 22,241, issued on Apr. 23, 1935, May 18, 1937 and Dec. 29, 1942, respectively, to Lefort) followed by hydration to give ethylene glycol.

More recently, dwindling petroleum reserves in conjunction with high price increases for petroleum placed an increased emphasis on the use of synthesis gas as a starting material for various chemicals such as methanol, formaldehyde and ethylene glycol. The advantage of synthesis gas is that it can be produced from raw materials other than petroleum such as natural gas or coal, and potentially from oil shale and tar sands.

An example of an industrial process for the production of ethylene glycol utilizing synthesis gas as a starting material is the reaction of formaldehyde with carbon monoxide and water at high pressures (over 300 atmospheres) in the presence of an acid catalyst to produce hydroxyacetic (glycolic) acid which is then reacted with methanol to give the methyl ester; the latter is then converted to the glycol by catalytic hydrogenation. See U.S. Pat. Nos. 2,316,564 issued Apr. 13, 1943 to Cockerill; 2,153,064 issued Apr. 4, 1939 to Larson; and 2,152,852, 2,285,448 and 2,331,094 issued Apr. 4, 1939, June 9, 1942 and Oct. 5, 1943, respectively, to Loder.

Another proposed process utilizing synthesis gas for the production of ethylene glycol is the reaction of methanol and carbon monoxide using a rhodium-catalyzed, high pressure process; see U.S. Pat. Nos. 4,115,428 issued to Vidal et al and 4,115,433 issued to Cosby et al on Sept. 19, 1978.

With respect to the type of process for the production of ethylene glycol disclosed and claimed herein, it should be noted the the oxidative dimerization or dehydrodimerization of a large variety of organic compounds by peroxides is very old art that was pioneered by the preeminent free radical theoretician M. S. Kharasch and his students. These studies became the foundations of much subsequent free radical chemistry. Kharasch et al in JACS 65, 15 1943 shows the dehydrodimerization of acetic acid to succinic acid with acetal peroxide in a 50 mole percent utilization selectivity based on acetyl peroxide, utilization selectively being defined as the moles of dehydrodimer product made divided by the moles of peroxide converted. Isobutyric acid produced tetramethylsuccinic acid in a 42.2 mole percent utilization selectivity. Kharasch et al in J. Org. Chem 10 386, 1945 show the ester methyl chloroacetate being dimerized to dimethyl dichlorosuccinate by acetyl peroxide in a 41 percent utilization selectivity. Kharasch et al in J. Org. Chem. 10 401, 1945 show the dimerization of cumene and ethylbenezene with acetyl peroxide in 61.9 mole percent and 32.1 mole percent respectively to their dehydrodimers. Wiles et al in I&E,C August 1949 page 1682 tell of the efficacy of di-t-butyl peroxide and 2,2-bis (t-butyl-peroxy) butane for the dimerization of cumene. The benzoate ester of benzyl alcohol was dimerized to the dibenzoate ester of the corresponding glycol, 1,2-diphenylethylene glycol, with di-t-butyl peroxide by Rust et al JACS 70, 3258 (1948).

The literature is replete with many other examples that produced the dehydrodimers at very low concentrations at utilization selectivities of generally from 20-50 mole percent based on the peroxide consumed. These selectivities are generally too low for the process to be considered for commercial development.

In connection with ethylene glycol, two teachings involving peroxide-induced reactions should be mentioned:

The first is described by Schwetlick et al, Angew. Chem. 72, 1960, No. 21, pages 779 and 780, and involves heating a mixture of di-tertiary-butyl peroxide and methanol in a molar ratio of 1:20 in an autoclave and/or under reflux for a period of 10 hours at 140° C. A 26 percent yield of ethylene glycol is reported, with the statement being made that an increase in the alcohol excess raises the yields.

The second and more important of such other reaction paths to ethylene glycol, in terms of its relevance to the present invention, is described by Oyama in J. Org. Chem. 30, July, 1965, pages 2429–2432. In particular, Oyama shows the reaction of 9 moles of methanol, 1.8 moles of 15 percent aqueous formaldehyde and 0.45 moles of t-butyl peroxide (ditertiary-butyl peroxide) at 140° C. for 12 hours to give 0.21 moles of ethylene glycol (Table I at the top of the right hand column on page 2430), with the statement being made immediately below Table I: "The yield of ethylene glycol in the reaction of formaldehyde with methanol is higher than that of t-butyl peroxide induced dimerization of methanol. This fact suggests that hydroxymethyl radical (D) adds to formaldehyde." Oyama describes in greater detail how this reaction was run and the products obtained, and contrasts it with the dehydrodimerization of methanol in the presence of t-butyl peroxide and the absence of formaldehyde, in the "Experimental" section beginning at page 2431 (see particularly the sections headed "Reaction of Methanol with Formaldehyde" and "Dimerization of Methanol" on page 2432).

The yields of ethylene glycol obtained by Oyama are fairly low. Oyama's only run with methanol—that involving the above-described reaction of methanol, aqueous formaldehyde and t-butyl peroxide at 140° C. for 12 hours—gave 1.86 weight percent of ethylene glycol, a yield too low for a commercially feasible process.

I have discovered, however, that the above-described reaction can be made commercially attractive by substantially decreasing the amount of organic peroxide employed, relative to the amounts of formaldehyde and methanol present, from that employed by Oyama. Moreover, increasing the amount of methanol and decreasing the amount of water, relative to the other components of the reaction mixture, in contrast to the amounts employed by Oyama, also appear to contribute to the production of higher yields of ethylene glycol. Thus, for example, heating a mixture of 78.5 weight percent of methanol, 1.5 weight percent of di-tertiary-butyl peroxide, 6.9 weight percent of formaldehyde and 13.1 weight percent of water at 155° C. for 2 hours gave a yield of 4.5 weight percent of ethylene glycol in the product mixture. This is equivalent to a yield of about 7.1 moles of ethylene glycol per mole of di-tertiary-butyl peroxide employed. (Oyama obtained 0.466 mole of ethylene glycol per mole of di-tertiary-butyl peroxide in his reaction).

In general, reaction feeds employed in practicing the present invention will contain no higher than about 6 weight percent, e.g. from about 0.25 to about 6 weight percent, and preferably no higher than about 3 weight percent, e.g. about 0.75 to 3 weight percent, of organic peroxide. In most cases, the feed will also contain from about 45 to 97 weight percent, preferably from about 80 to about 85 weight percent, of methanol, from about 0.5 to about 13 weight percent, preferably from about 2 to about 12 weight percent, of formaldehyde, and from about 0.5 to about 35 weight percent, preferably from about 2 to about 10 weight percent, of water.

The reaction will generally be carried out at a temperature of from about 100° C. to about 200° C., preferably at from about 125° C. to about 175° C. at a residence time of no higher than about 8 hours, usually from about 0.25 hours to about 8 hours, and preferably from about 0.5 to about 4 hours. Generally, the higher the temperature, the lower the reaction time necessary to bring the reaction to a desired state of completion. There is little or no criticality in the pressure at which the reaction is carried out. Pressures of between autogenous pressure (in a closed reactor) to about 600 psig (with pressures being chosen when a reactor open to the atmosphere is used which are sufficient to keep the reactants, and particularly methanol, from being driven off) can be utilized.

The organic peroxide employed in the process of this invention has the formula

R-O-O-R¹ wherein R and R¹ are each an alkyl or aralkyl group having 3 to 12 carbon atoms. Organic peroxides which may be employed are, for example, di-tertiarybutyl peroxide, di-cumyl peroxide, tertiary-butyl cumyl peroxide and tertiarybutyl ethylbenzyl peroxide. The preferred organic peroxide is di-tertiary-butyl peroxide.

The reaction may be carried out batchwise, wherein a reactor such as a stirred autoclave is charge with the initial reaction mixture which is then subjected to reaction and after which the entire reaction mixture is withdrawn and purified, semi-continuously, in which the initial reaction mixture is charged and product mixture withdrawn intermittently from the reactor, or continuously, wherein the reaction mixture is charged continuously and product mixture withdrawn continuously from the reactor. The product mixture may then be purified using conventional techniques such as distillation or solvent extraction to obtain the ethylene glycol in desired purity and by-products such as tertiary-butyl alcohol, methylal, methyl formate, glycerine and acetone.

In some cases, it may be desirable to add a small amount of a base such as sodium bicarbonate to the initial charge mixture for the purpose of neutralizing any acid initially present or formed during the reaction for the purpose of minimizing the formation of methylal. Since methylal is not an ethylene glycol precursor, its formation is believed to lower the productivity of the process on a once-through basis.

The process of this invention results in higher yields of ethylene glycol expressed in terms of weight percent of the product mixture, and substantially higher yields of ethylene glycol if expressed in terms of moles of ethylene glycol per mole of organic peroxide consumed in the reaction, than would be predictable from the prior art. Thus, utilizing the process of this invention, ethylene glycol yields of at least about 2.5 or 3 percent, and in many cases 3.5 to 7 or higher weight percent of the product mixture, and at least about 1 or 2, in many cases from about 3 to about 11 moles of ethylene glycol per mole of organic peroxide consumed in the reaction, may be obtained.

EXAMPLES 1–31

An initial reaction mixture containing methanol (MeOH), di-tertiary-butyl peroxide (DtBP), formaldehyde ($CH_2O$), and water ($H_2O$) was charged to a stirred autoclave in the following manner: all but about 20 weight percent of the methanol in the initial charge, formaldehyde either as a mixture containing about 55 weight percent of formaldehyde, about 35 weight percent of methanol, and about 10 weight percent of water or as an aqueous solution of about 35 weight percent of formaldehyde and about 65 weight percent of water, and any additional water in the charge not present in the charged formaldehyde solution, were added to a stirred autoclave at room temperature. The mixture was then heated up to reaction temperature and a solution of di-tertiary-butyl peroxide in the remaining 20 weight percent of methanol was added to the autoclave to initiate the reaction. A reaction pressure of 350 psig was maintained with nitrogen. After the prescribed reaction time, the product mixture was removed from the autoclave and analyzed for ethylene glycol (EG).

The results of these examples are shown in Table I which sets out the composition of the initial charge, the temperature and reaction time employed for the reaction, and the amount of ethylene glycol produced in each example, both in terms of weight percent of the product mixture and in terms of moles of product per mole of di-tertiary-butyl peroxide consumed in the reaction.

TABLE I

| | Initial Charge, wt. % | | | | Process Conditions | | Product | |
|---|---|---|---|---|---|---|---|---|
| Example | MeOH | DtBP | $CH_2O$ | $H_2O$ | Temp, °C. | Reaction Time, hrs. | EG, wt % | moles EG / mole DtBP |
| 1 | 81.7 | 1.5 | 11.2 | 5.6 | 175 | 2.0 | 3.6 | 5.6 |
| 2 | 81.7 | 1.5 | 11.2 | 5.6 | 175 | 2.0 | 3.8 | 5.9 |
| 3 | 80.2 | 3.0 | 11.2 | 5.6 | 175 | 2.0 | 5.3 | 4.2 |
| 4 | 80.2 | 3.0 | 11.2 | 5.6 | 174 | 2.0 | 5.4 | 4.2 |
| 5 | 82.45 | 0.75 | 11.2 | 5.6 | 175 | 2.0 | 2.7 | 8.2 |
| 6 | 77.2 | 6.0 | 11.2 | 5.6 | 176 | 2.0 | 6.7 | 2.5 |
| 7 | 90.6 | 1.5 | 5.6 | 2.3 | 175 | 2.0 | 3.4 | 5.2 |
| 8 | 69.7 | 1.5 | 19.2 | 9.6 | 175 | 2.0 | 2.4 | 3.7 |
| 9 | 81.7 | 1.5 | 11.2 | 5.6 | 154 | 2.0 | 4.4 | 6.9 |
| 10 | 81.7 | 1.5 | 11.2 | 5.6 | 190 | 2.0 | 3.2 | 4.9 |
| 11 | 81.7 | 1.5 | 11.2 | 5.6 | 190 | 2.0 | 3.4 | 5.2 |
| 12 | 85.0 | 1.5 | 11.2 | 2.8 | 174 | 2.0 | 3.7 | 5.6 |
| 13 | 76.1 | 1.5 | 11.2 | 11.2 | 175 | 2.0 | 3.1 | 4.7 |
| 14 | 93.4 | 1.5 | 2.8 | 3.0 | 175 | 2.0 | 1.9 | 2.9 |
| 15 | 85.0 | 1.5 | 11.2 | 2.3 | 156 | 2.0 | 4.6 | 7.0 |
| 16 | 85.0 | 1.5 | 11.2 | 2.3 | 156 | 2.0 | 3.7 | 5.8 |
| 17 | 83.5 | 3.0 | 11.2 | 2.3 | 155 | 2.0 | 5.8 | 4.5 |
| 18 | 80.5 | 6.0 | 11.2 | 2.3 | 155 | 3.0 | 6.9 | 2.6 |
| 19 | 85.8 | 0.75 | 11.2 | 2.3 | 155 | 2.0 | 3.4 | 10.5 |
| 20 | 78.5 | 1.5 | 6.9 | 13.1 | 155 | 2.0 | 4.5 | 7.1 |
| 21 | 91.8 | 1.5 | 5.60 | 1.14 | 155 | 2.0 | 4.5 | 7.0 |
| 22 | 95.1 | 1.5 | 2.8 | 0.57 | 155 | 2.0 | 2.9 | 4.6 |
| 23 | 75.4 | 1.44 | 19.22 | 3.91 | 143 | 4.0 | 2.6 | 4.2 |
| 24 | 85.0 | 1.5 | 11.2 | 2.3 | 142 | 4.0 | 4.5 | 7.5 |
| 25 | 75.4 | 1.44 | 19.22 | 3.9 | 155 | 2.0 | 3.4 | 5.5 |
| 26 | 85.0 | 1.35 | 11.2 | 2.3 | 142 | 4.0 | 4.5 | 7.5 |
| 27 | 85.0 | 1.50 | 11.2 | 2.3 | 176 | 1.0 | 4.0 | 6.4 |
| 28 | 85.0 | 1.50 | 11.2 | 2.3 | 174 | 2.0 | 3.7 | 5.6 |
| 29 | 85.0 | 1.50 | 11.2 | 2.3 | 192 | 2.0 | 3.7 | 5.7 |
| 30 | 81.7 | 1.5 | 11.2 | 5.6 | 154 | 2.0 | 4.4 | 6.9 |
| 31 | 76.1 | 1.5 | 11.2 | 11.2 | 153 | 2.0 | 3.9 | 6.2 |

EXAMPLES 32-64

Charges of the various feed compositions comprising methanol (MeOH), di-tertiary-butyl peroxide (DtBP) or di-cumyl peroxide (DCP) in Examples 40 and 41, formaldehyde ($CH_2O$) as a mixture of 36 weight percent $CH_2O$, about 14 weight percent MeOH and 50 percent water ($H_2O$), sodium bicarbonate ($NaHCO_3$) and any additional water in the charge not present in the charged formaldehyde solution, were prepared and charged to a 304 S.S. Hoke reactor at atmospheric pressure. The reactor was capped and placed in a thermostated oil bath held at the stated reaction temperature and allowed to react for the stated reaction time at autogenous pressure. After the reaction time was completed, the reactor was cooled by quenching, vented, discharged and analyzed by gas chromotography for contained ethylene glycol.

The results of these examples are shown in Table II.

TABLE II

| | Initial Charge, wt. % | | | | | Process Conditions | | Product | |
|---|---|---|---|---|---|---|---|---|---|
| Example | MeOH | DtBP | $CH_2O$ | $H_2O$ | $NaHCO_3$ | Temp, °C. | Reaction Time, hrs. | EG, wt % | moles EG / mole DtBP |
| 32 | 84.07 | 1.23 | 6.14 | 8.53 | .026 | 155 | 1 | 5.18 | 9.9 |
| 33 | 81.77 | 1.19 | 7.12 | 9.89 | .025 | 155 | 1 | 5.29 | 10.5 |
| 34 | 82.35 | 2.98 | 6.13 | 8.51 | .026 | 155 | 1 | 6.26 | 4.9 |
| 35 | 80.07 | 2.89 | 7.12 | 9.89 | .025 | 155 | 1 | 6.72 | 5.5 |
| 36 | 79.36 | 5.97 | 6.13 | 8.51 | .026 | 155 | 1 | 7.70 | 3.0 |
| 37 | 77.16 | 5.78 | 7.13 | 9.90 | .025 | 155 | 1 | 7.71 | 3.1 |
| 38 | 84.02 | 1.23 | 6.17 | 8.57 | .013 | 155 | 1 | 4.89 | 9.4 |
| 39 | 81.59 | 1.20 | 7.2 | 10.0 | .013 | 155 | 1 | 5.00 | 9.8 |
| 40 | 82.65 | 3.0[1] | 6.0 | 8.33 | .016 | 155 | 1 | 3.49 | 5.1 |
| 41 | 82.61 | 3.0[1] | 6.0 | 8.33 | .063 | 155 | 1 | 3.36 | 4.9 |
| 42 | 92.04 | 1.38 | 2.75 | 3.82 | .015 | 155 | 1 | 3.12 | 5.3 |
| 43 | 89.41 | 1.33 | 3.87 | 5.38 | .014 | 155 | 1 | 3.93 | 7.0 |
| 44 | 92.0 | 3.49 | 1.88 | 2.61 | .015 | 155 | 1 | 3.41 | 2.3 |
| 45 | 89.99 | 3.43 | 2.75 | 3.82 | .015 | 155 | 1 | 4.43 | 3.0 |
| 46 | 84.6 | 2.5 | 5.4 | 7.5 | — | 155 | 1 | 5.51 | 5.2 |
| 47 | 85.85 | 1.25 | 5.4 | 7.5 | — | 155 | 1 | 4.48 | 8.4 |
| 48 | 86.47 | .625 | 5.4 | 7.5 | — | 155 | 1 | 3.47 | 13.1 |
| 49 | 84.6 | 2.5 | 5.4 | 7.5 | — | 140 | 3 | 5.99 | 5.6 |
| 50 | 85.85 | 1.25 | 5.4 | 7.5 | — | 140 | 3 | 4.60 | 8.7 |
| 51 | 86.47 | .625 | 5.4 | 7.5 | — | 140 | 3 | 3.37 | 12.7 |
| 52 | 84.6 | 2.5 | 5.4 | 7.5 | — | 175 | .25 | 5.02 | 4.7 |
| 53 | 85.85 | 1.25 | 5.4 | 7.5 | — | 175 | .25 | 3.67 | 6.9 |
| 54 | 86.47 | .625 | 5.4 | 7.5 | — | 175 | .25 | 2.66 | 10.0 |
| 55 | 80.85 | 1.25 | 5.4 | 12.5 | — | 155 | 1 | 4.1 | 7.7 |
| 56 | 80.82 | 1.25 | 5.4 | 12.5 | .025 | 155 | 1 | 4.25 | 8.0 |
| 57 | 81.6 | 1.25 | 3.6 | 13.5 | .05 | 155 | 1 | 3.19 | 6.0 |
| 58 | 81.73 | 6.24 | 5.03 | 6.99 | .014 | 135 | 1 | 3.63 | —[2] |

TABLE II-continued

| Example | Initial Charge, wt. % | | | | | Process Conditions | | Product | |
|---|---|---|---|---|---|---|---|---|---|
| | MeOH | DtBP | CH$_2$O | H$_2$O | NaHCO$_3$ | Temp, °C. | Reaction Time, hrs. | EG, wt % | moles EG / mole DtBP |
| 59 | 81.73 | 6.24 | 5.03 | 6.99 | .014 | 135 | 2 | 5.40 | —[2] |
| 60 | 81.73 | 6.24 | 5.03 | 6.99 | .014 | 135 | 3 | 6.34 | —[2] |
| 61 | 81.73 | 6.24 | 5.03 | 6.99 | .014 | 135 | 4 | 6.80 | —[2] |
| 62 | 81.73 | 6.24 | 5.03 | 6.99 | .014 | 125 | 1 | 2.24 | —[2] |
| 63 | 81.73 | 6.24 | 5.03 | 6.99 | .014 | 125 | 2 | 3.69 | —[2] |
| 64 | 81.73 | 6.24 | 5.03 | 6.99 | .014 | 125 | 4 | 5.39 | —[2] |

[1] di-cumyl peroxide used in place of di-tertiary butyl peroxide
[2] Examples 58 to 64 were partial conversion runs in which the extent of DtBP conversions were not analytically determined. However, stability of DtBP is such that any unconverted DtBP could be recycled.

As can be seen from the data in the tables the amount of ethylene glycol produced in the examples varied between 1.9 and 7.71 weight percent of the product, all higher and most considerably higher than the 1.86 weight percent disclosed by Oyama in the article cited previously, and 2.3 to 13.1 moles of ethylene glycol per mole of organic peroxide charged to the reaction, all substantially higher than the 0.466 mole of ethylene glycol per mole of di-tertiary-butyl peroxide disclosed by Oyama.

What is claimed is:

1. In a process for producing ethylene glycol by reacting methanol, an organic peroxide, and formaldehyde in the presence of water, said organic peroxide having the formula R-O-O-R$^1$ wherein R and R$^1$ each is an alkyl or aralkyl group containing 3 to 12 carbon atoms, the improvement comprising utilizing no more than about 6 weight percent of organic peroxide and an amount of water ranging from about 0.5 to about 35 weight percent, based on the total weight of methanol, organic peroxide, formaldehyde and water present, in the initial reaction mixture.

2. The process of claim 1 wherein the organic peroxide is di-tertiary-butyl peroxide.

3. The process of claim 2 wherein no more than about 3 weight percent of di-tertiary-butyl peroxide is utilized in the initial reaction mixture.

4. The process of claim 1 wherein the reaction time is no greater than about 8 hours.

5. The process of claim 2 wherein the initial reaction mixture contains from about 45 to about 97 weight percent of methanol, from about 0.25 to about 6 weight percent of di-tertiary-butyl peroxide, from about 0.5 to about 13 weight percent of formaldehyde, and from about 0.5 to about 35 weight percent of water, the reaction temperature is from about 100 to about 200° C., and the reaction time is from about 0.25 to about 8 hours.

6. The process of claim 5 wherein the initial reaction mixture contains about 65 to 90 weight percent of methanol, from about 0.75 to about 3 weight percent of di-tertiary-butyl peroxide, from about 2 to about 12 weight percent of formaldehyde, and from about 2 to about 10 weight percent of water, the product temperature is from about 125 to about 175° C. and the reaction time is from about 0.5 to about 4.0 hours.

7. The process of claim 2 wherein the amount of ethylene glycol produced in the reaction is at least about 3 weight percent of the product mixture and at least about 1 mole per mole of di-tertiary-butyl peroxide charged to the reaction.

8. The process of claim 7 wherein the amount of ethylene glycol produced in the reaction is at least about 5 weight percent of the product mixture and at least about 3 moles per mole of di-tertiary-butyl peroxide charged to the reaction.

* * * * *

UNITED STATES PATENT AND TRADEMARK OFFICE
CERTIFICATE OF CORRECTION

PATENT NO. : 4,337,371
DATED : June 29, 1982
INVENTOR(S) : JOHN KOLLAR

It is certified that error appears in the above–identified patent and that said Letters Patent are hereby corrected as shown below:

On the title page, after "Assignee," change "Celanese Corporation, N.Y." to --Redox Technologies, Inc., Wyckoff, N.J.--.

Signed and Sealed this

Second Day of November 1982

[SEAL]

Attest:

GERALD J. MOSSINGHOFF

Attesting Officer

Commissioner of Patents and Trademarks